Figure 1:
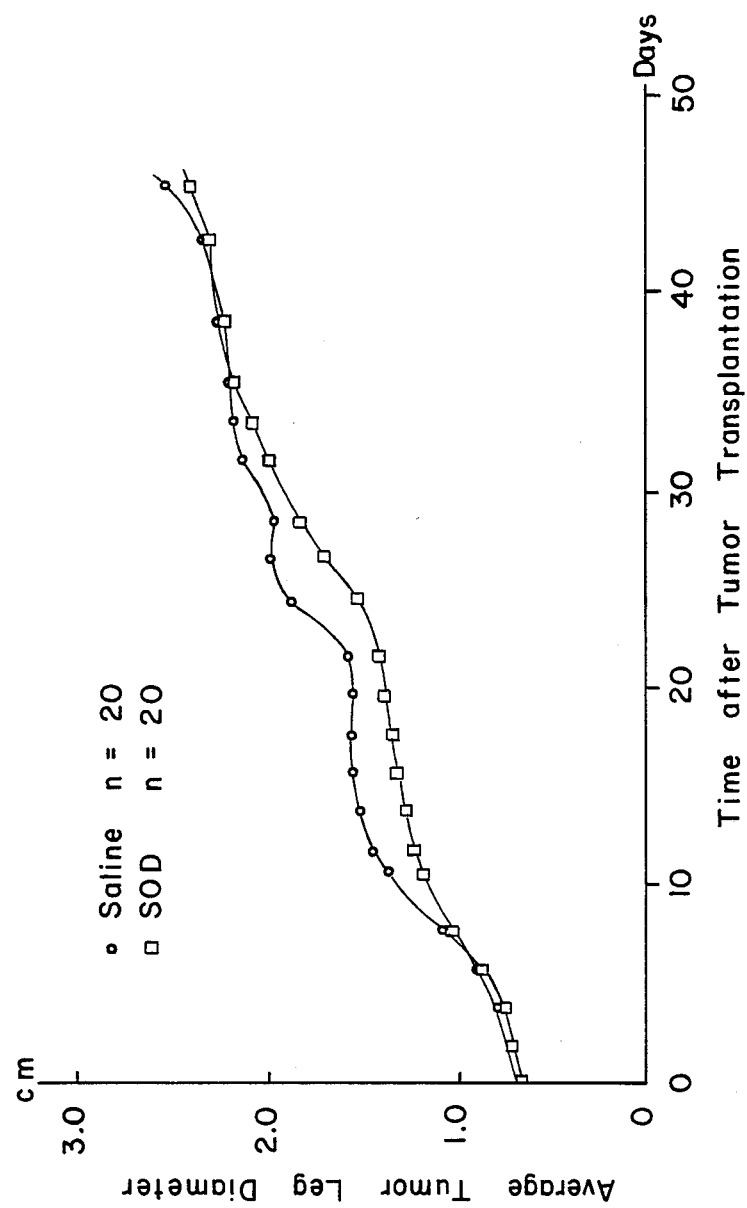
Figure 2:
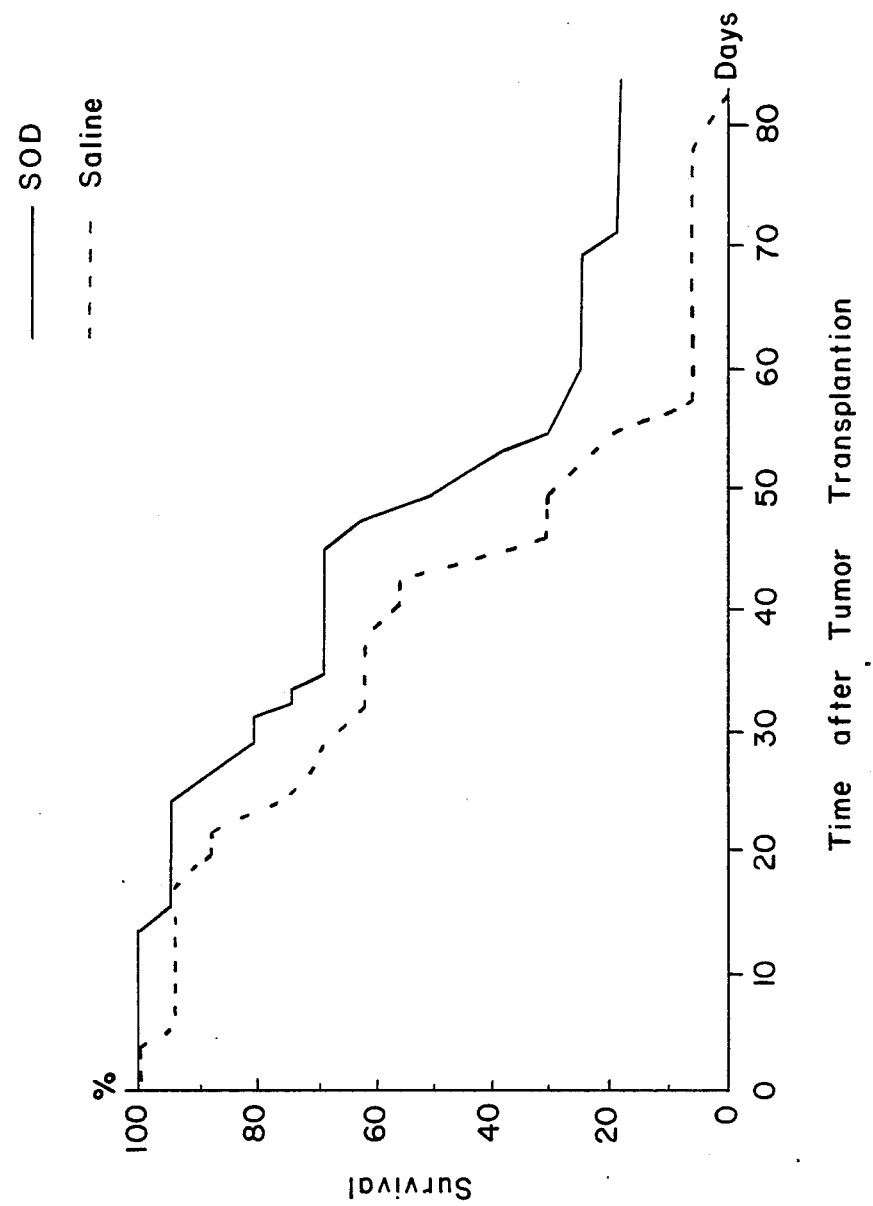
Figure 3:
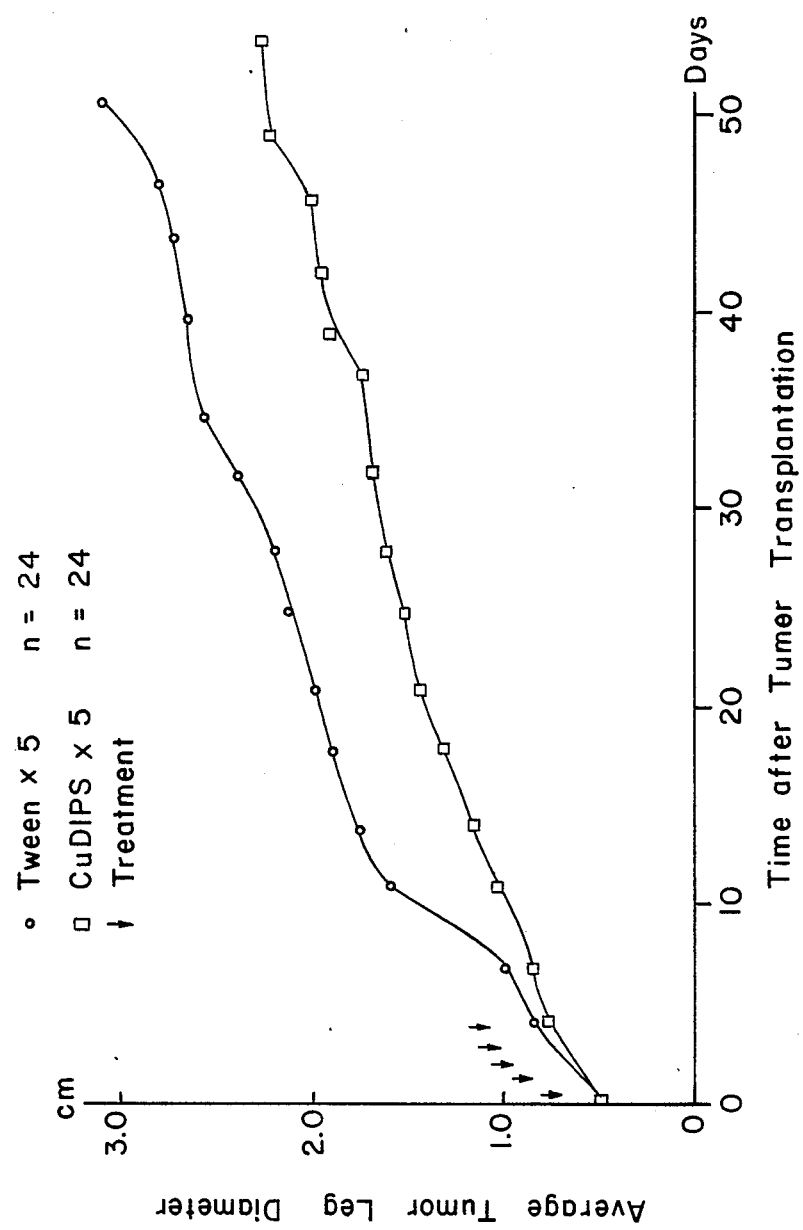
Figure 4:
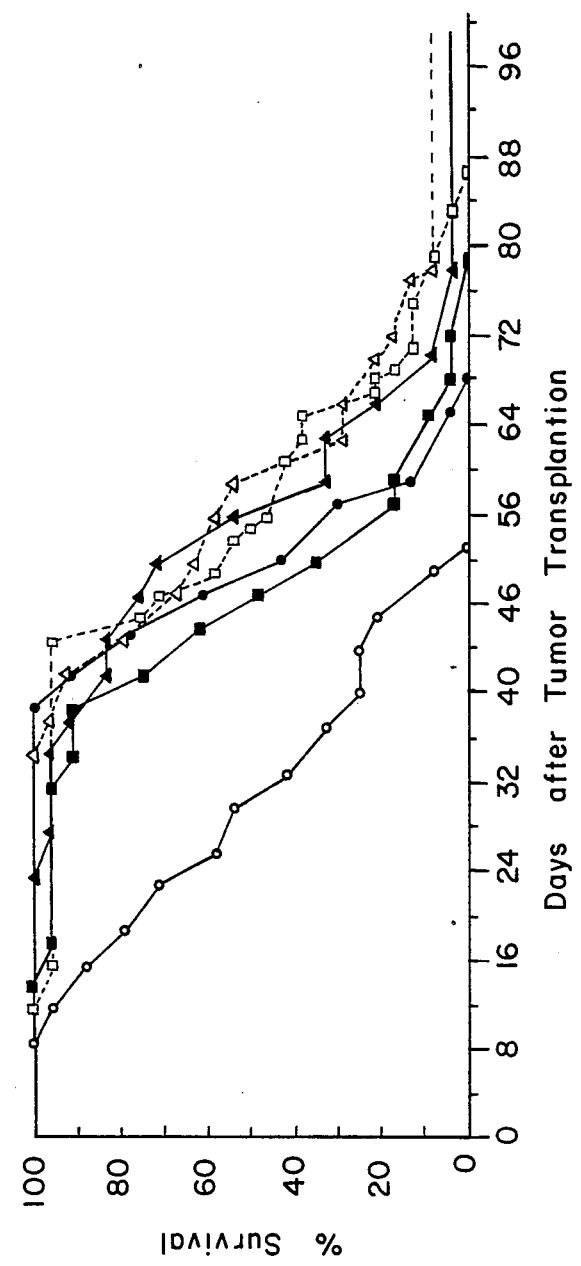
Figure 5:
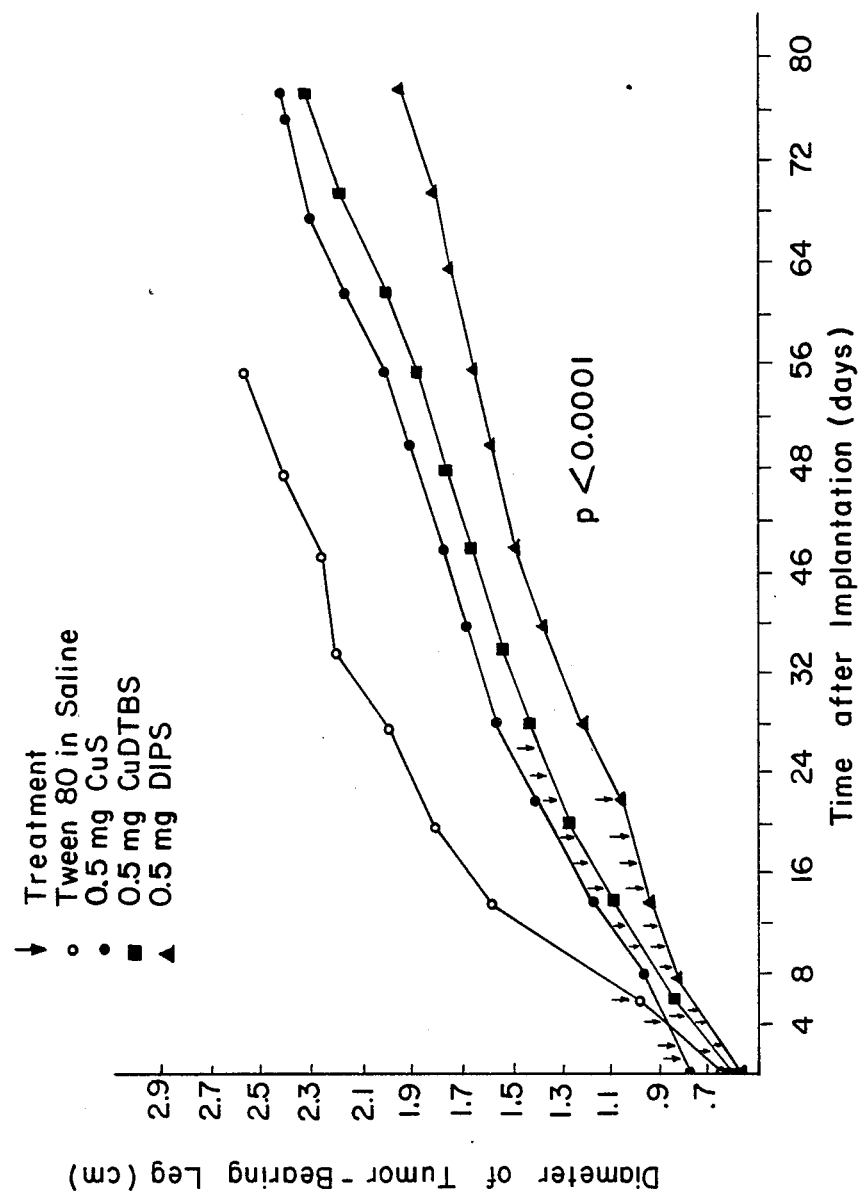
Figure 6:
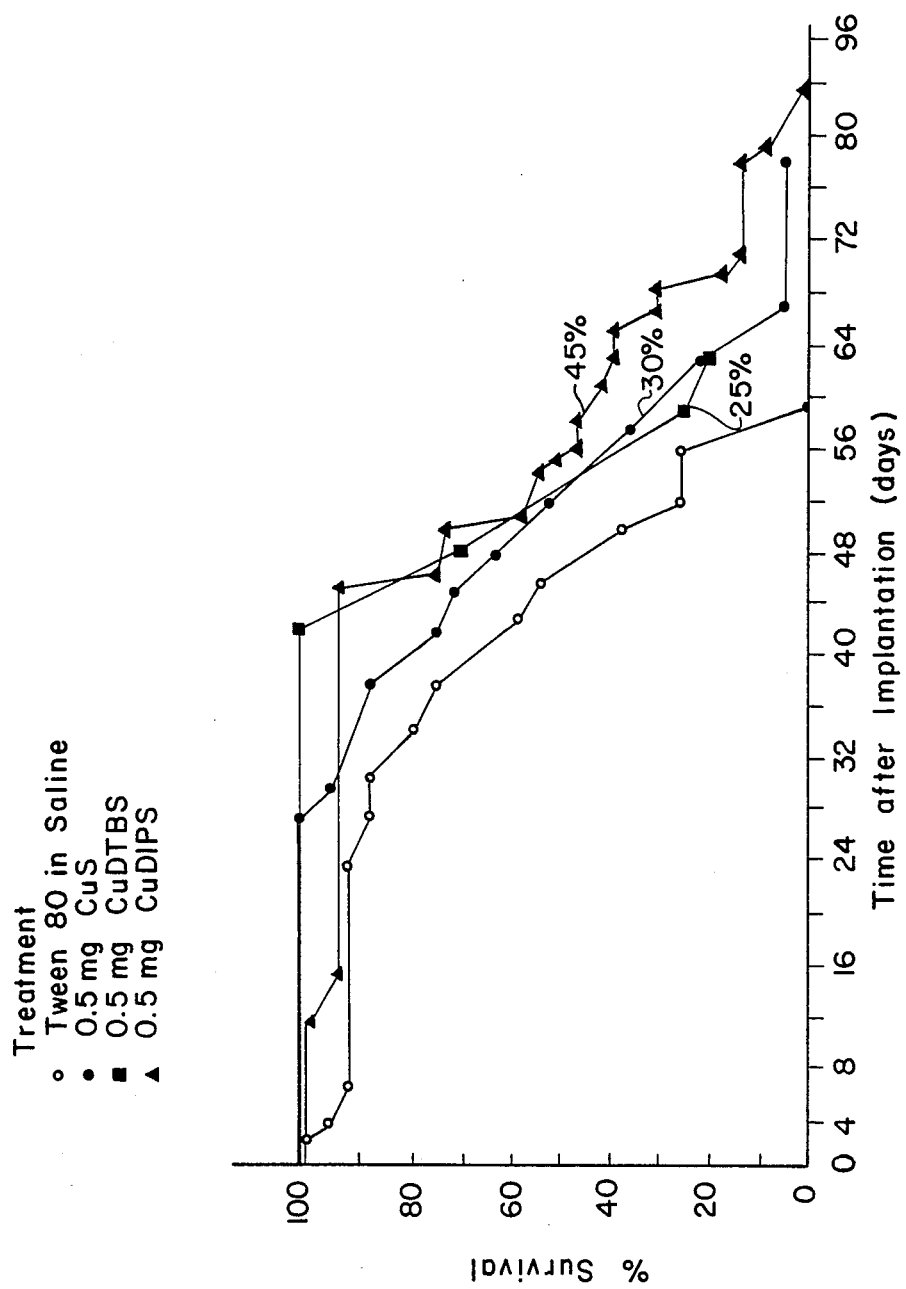
Figure 7:
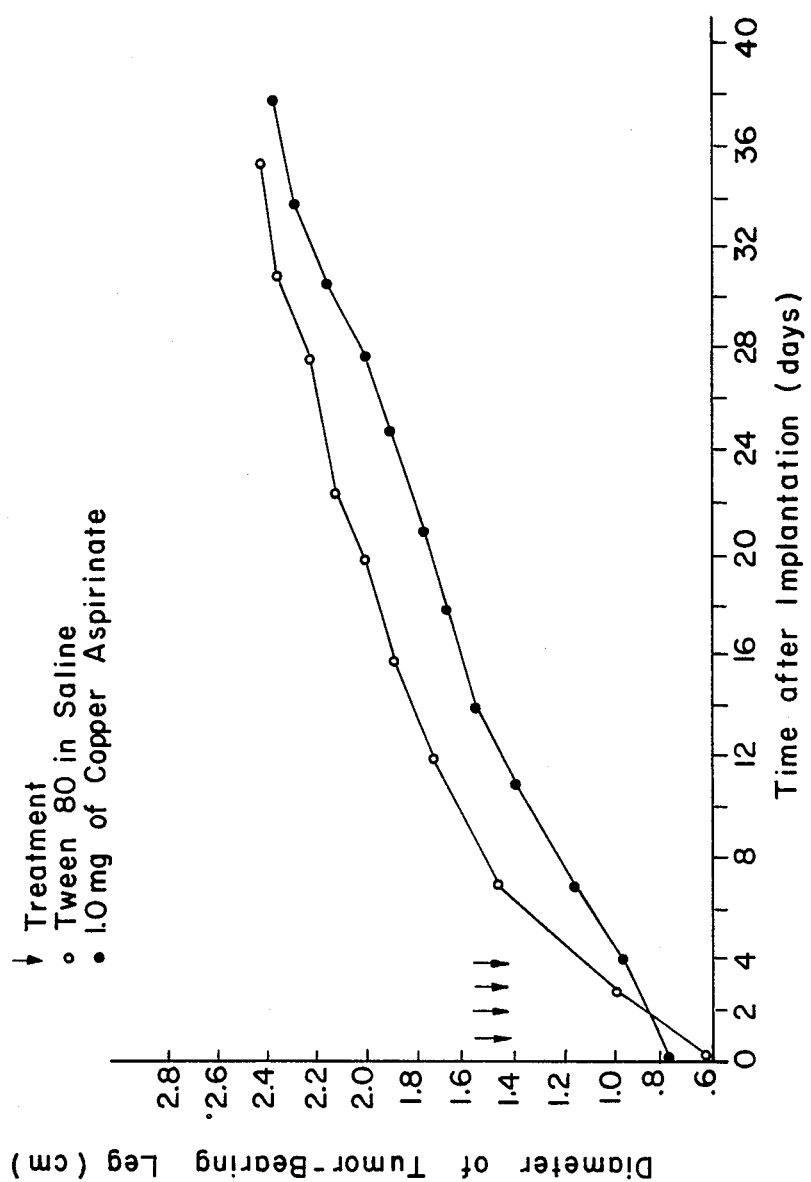
Figure 8:
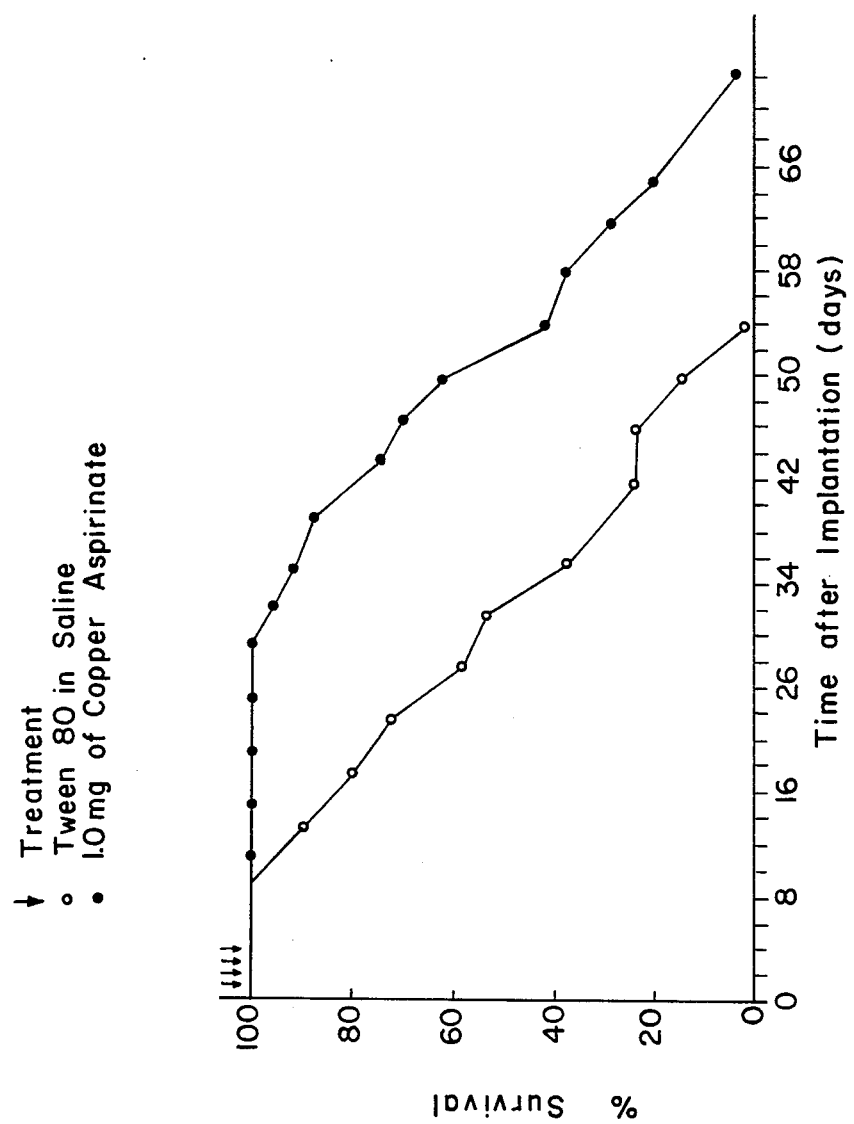
Figure 9:
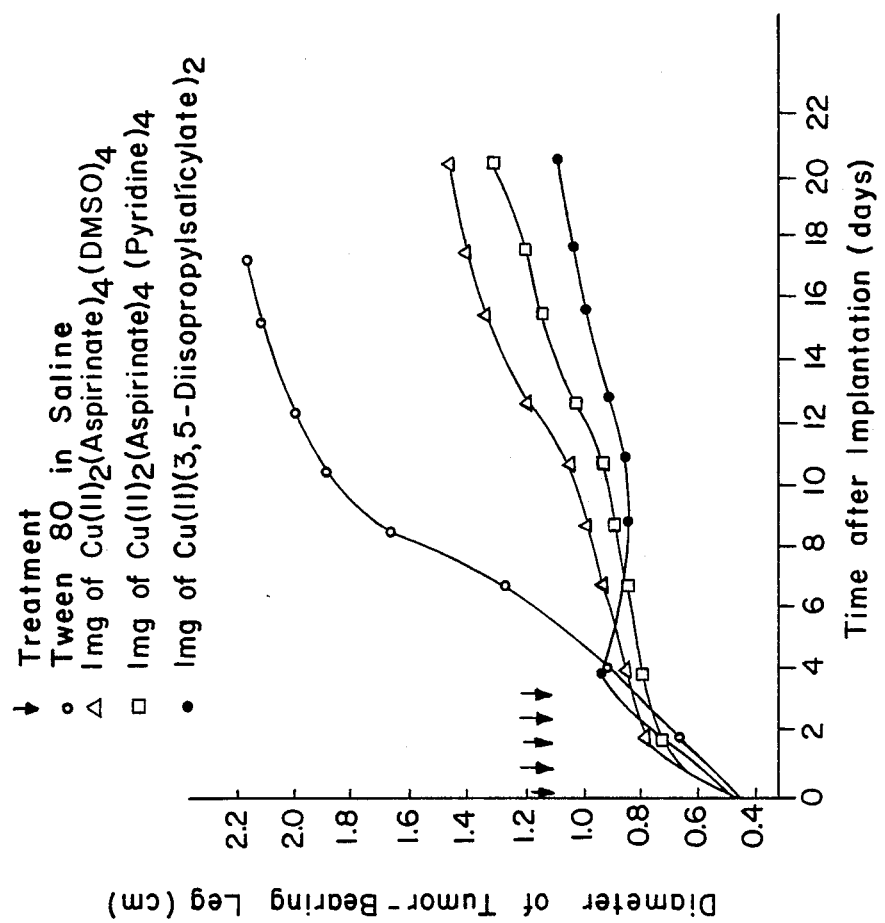

United States Patent [19]

Sorenson et al.

[11] Patent Number: 4,952,607

[45] Date of Patent: Aug. 28, 1990

[54] COPPER COMPLEX FOR TREATING CANCER

[75] Inventors: John R. J. Sorenson, Little Rock, Ark.; Larry W. Oberley, Iowa City, Iowa

[73] Assignee: International Copper Research Association, Inc., New York, N.Y.

[21] Appl. No.: 823,968

[22] Filed: Jan. 30, 1986

Related U.S. Application Data

[63] Continuation of Ser. No. 382,557, May 27, 1982.

[51] Int. Cl.$^5$ ............................................... C07F 1/08
[52] U.S. Cl. ................................... 514/589; 514/188; 514/499
[58] Field of Search .................... 514/499, 188, 589

[56] References Cited

U.S. PATENT DOCUMENTS

| | | | |
|---|---|---|---|
| 3,884,949 | 5/1975 | Eicke et al. | 260/438.1 X |
| 4,221,785 | 9/1980 | Sorenson | 424/230 |
| 4,287,190 | 9/1981 | Boettcher et al. | 260/438.1 X |
| 4,373,953 | 2/1983 | Deinet et al. | 424/294 X |

OTHER PUBLICATIONS

Chemical Abstracts 69 113013z(1968).
Chemical Abstracts 84 38591r(1976).
Chemical Abstracts 85 116777t(1976).
Beauchamp and Fridovich, Anal. Biochem. 44:276-287 (1971).
Georgieff, Science 173:537-539 (1971).
Leuthauser et al., J. Nat'l Cancer Inst. 66:1077-1081 (Jun., 1981).
Oberley, "Superoxide Dismutose and Cancer" vol. 2, ch. 6, CRC Press (1982).
Oberley & Beuttner, Cancer Res. 39:1141-1149 (1979).
Oberley et al., in Roles of Copper and Other Essential Mettaloelements in Inflammatory Diseases, Humana Press, Clifton, N.J. pp. 423-433 (1982).
Sorenson, J. Med. Chem. 19:135-148 (1976).
Sorenson, Inflammation 1:317-331 (1976).
Westman and Marklund, Cancer Res.: 41:2962-2966 (1981).
Sorenson, "Therapeutic Uses of Copper" in Copper in the Environment, Part II, Nriagu, ed., Wiley & Sons, pp. 83-162 (1979).
Leuthauser, S. W., 1979, Antitumor Activities of Superoxide Dismutase and Copper Coordination Compounds, Ph.D. Thesis; Iowa City: University of Iowa.

Primary Examiner—Paul F. Shaver
Attorney, Agent, or Firm—Pennie & Edmonds

[57] ABSTRACT

The present invention relates to copper complexes exhibiting superoxide dismutase-like activity in mammalian cells. The copper complexes, which act as superoxide radical ($O_2^-$) scavengers, are used in treating cancer by replacing the lost superoxide dismutase activity which characterizes tumor systems. The low molecular weight and lipid solubility of the copper complexes facilitate penetration of cell membranes. Depending upon the specific type of copper complex used, treatment may result in decreased tumor growth, increased survival of the host organism, decreased tumor metastasis or induced morphological differentiation of cancerous cells. The copper complexes used according to the invention include copper salicylate complexes, their solvates as well as mixtures thereof. A method for the treatment of cancer using these copper complexes is also disclosed.

18 Claims, 9 Drawing Sheets

COPPER COMPLEX FOR TREATING CANCER

This is a continuation of application Ser. No. 382,557, filed May 27, 1982.

TECHNICAL FIELD

The present invention relates to a copper complex for treating cancer by decreasing tumor growth, increasing survival of a host, decreasing tumor metastasis and inducing morphological differentiation of cancerous cells. A method for treatment of cancer using this complex is also disclosed.

BACKGROUND OF THE INVENTION

Oxygen toxicity in aerobic organisms has been widely studied. The enzyme SOD—superoxide dismutase—plays a significant role in the defense against such toxicity.

Superoxide radical ($O_2^-$) is generated in various biological reactions; this free radical anion is potentially damaging either because it is extremely reactive or because it can generate highly toxic species like OH. Superoxide dismutase catalyses the dismutation of $O_2^-$:

$$2H^+ + O_2^- O_2^- \rightarrow H_2O_2 + O_2$$

In a mammalian cell, two types of SOD are found. One contains both copper and zinc and is located in the cytosol and periplasmic space of the mitochondria (CuZnSOD). The other enzyme contains manganese and is present in the matrix of the mitochondria (MnSOD). All normal mammalian cell types investigated contain these two types of the enzyme, except erythrocytes which lack MnSOD. However, in nearly all of the tumor systems studied so far, the level of CuZnSOD and MnSOD activities were diminished. There are a few exceptions for CuZnSOD activity, but no exception has been found in the case of MnSOD activity. In many tumor samples, the MnSOD content is reduced to a level where it cannot be detected. Superoxide, on the other hand, is apparently still being generated in tumor mitochondria, and conceivably, the presence of this reactive species coupled with the relative lack of MnSOD could lead to changes in key subcellular structures due to the presence of oxygen derived chemical species. These changes may, in turn, contribute to the cancer phenotype.

The role of SOD in cancer has been the topic of a recent review in Oberley, L. W. and Buettner, G. R., *The Role of Superoxide Dismutase in Cancer: A Review*, Cancer Res. 39:1141-1149 (1979) and in 2 Oberley, L. W., *Superoxide Dismutase*, Chapter 6, (CRC Press 1982), both hereby incorporated by reference. SOD activities for numerous cancer types are specified.

Reduced MnSOD activity has been found in over fifty human, rat, mouse, spontaneous, transplanted virally-induced, chemically-induced, in vivo and in vitro tumors. In addition, both CuZnSOD and MnSOD activities in over thirty types of human tumors have been found to be less than those in control organs, Westman, N. G. and Marklund, S. L., Copper and Zinc-Containing Superoxide Dismutase and Manganese-Containing Superoxide Dismutase in Human Tissues and Human Malignant Tumors, Cancer Res. 41:2962(1981), hereby incorporated by reference. Thus, it has been demonstrated that loss of SOD activity is characteristic of a wide variety of human tumors and is not a phenomenon restricted to mouse and rat tumors. Examples of cancer types characaterized by low SOD activity levels include: Morris hepatomas, H6 hepatoma, Novikoff hepatoma, C3H carcinoma, Lewis lung carcinoma, Walker carcinoma, Mammary adenocarcinoma, Ehrlich ascites, EL-4 ascites, Guerin $T_R$ ascites, S91 melanoma, B16 melantic melanoma, Sarcoma 180, L1210 leukemia, L1210/6MP lymphoid leukemia, L1210/5FU lymphoid leukemia, P388 lymphoid leukemia, L1210/0 lymphoid leukemia, and Manning leukemia. This theory of excess free radicals with a deficiency of free radical scavengers in cancer cells has also been proposed by Georgieff, K. K., *Free Radical Inhibitory Effect of Some Anticancer Compounds*, Science 173:537-539 (1971), hereby incorporated by reference. Georgieff showed that various types of chemotherapeutic agents exhibit free radical inhibitory activity.

The present invention seeks to overcome the problems and disadvantages of the prior art. It has been discovered that copper complexes, which themselves act as $O_2^-$ scavengers, allow the neoplastic cell to revert to its non-cancerous phenotype. These complexes also inhibit cancer cell growth in vivo, thereby prolonging the survival of tumor-bearing host organisms. Tumor metastasis is also reduced. The discovery is not only a significant advance but also an unexpected discovery in the art of treating cancer.

DISCLOSURE OF INVENTION

Native SOD has a molecular weight of about 32,000 and, as a result, does not penetrate well into cell membranes. Cu(II) (3,5-diisopropylsalicylate)$_2$, CuDIPS, and other copper salicylate complexes are also $O_2^-$ scavengers and have a molecular weight that facilitates penetration into cell membranes. Their smaller molecular size (molecular weight between about 340 and about 1000, preferably between about 340 and about 600 for copper salicylate complexes and molecular weight between about 845 and about 1800, preferably between about 845 and about 1400 for copper acetylsalicylate complexes), that is, low molecular weight, and their lipid solubility allow better penetration of cell membranes, mitochondrial membranes and organelles. See Leuthauser, W. C., Oberley, L. W., Oberley, T. D., Sorenson, J. R. J., Ramakrishna, K., *Antitumor Effect of a Copper Coordination Compound With Superoxide Dismutase-Like Activity*, JNCI 66:1077-1081 (1981), hereby incorporated by reference. Thus, CuDIPS can mimic the action of lost SOD activity in tumor cells. The use of copper salicylate complexes, their solvates, as well as mixtures thereof, for the treatment of cancer according to this invention is advantageous in that the overall treatment mechanism does not, as with various known methods, involve only cytotoxicity but, instead, focuses on the replacement of lost SOD activity in tumor cells to effectively halt cell division and subsequent tumor growth. Such a non-cytotoxic approach to cancer therapy allows a continued regimen of treatment which is not, as with methods using cytotoxic compounds, limited by potential compounding of toxic effects.

This invention involves the effect of compounds with SOD activity on tumor growth and survival of tumor bearing mammals. Natural SOD and the subject copper salicylate complexes were found to have surprisingly different effects on these parameters.

Low SOD activity, which is defined as SOD activity below that exhibited in a given normal, non-cancerous cell, characterizes various types of cancer. Copper salicylate complexes, their solvates, as well as mixtures thereof, are useful in treating such types of cancer.

The purpose of tumor therapy is to eliminate tumor or to retard its growth, prevent metastasis and at the same time, prolong survival of a host. Inhibition of tumor metastasis is an important parameter in cancer control. Most primary tumors can be easily treated by various therapy regimens, but metastasis is usually difficult to prevent.

The tumor model used in the following experiment is Ehrlich carcinoma cells, which metastasized to the lungs, forming macroscopic nodules. Microscopic metastases are observed as early as the 10th day after transplantation of tumor cells in Tween 80-saline treated control animals. When mice treated with 5 daily doses of CuDIPS were killed on the 45th day after transplantation, only microscopic nodules were observed in the lungs. CuDIPS had delayed the process of metastasis in these Ehrlich tumor mice. However, lung metastases were the cause of death of these treated mice. Prolonged treatment further increased survival, possibly by suppressing metastases longer and thereby retarding tumor growth.

The results of the experimentation of this invention indicate that CuDIPS does indeed exert in vivo antitumor activity in the solid form of Ehrlich carcinoma. A greater effect was observed with an increased number of treatments when the total dose did not exceed $LD_{50}$ of the compound. It has also been observed that in vitro, CuDIPS inhibits growth of cultured neoplastic cells and induces morphological differentiation in cultured neuroblastoma cells.

It has also been discovered that cancer types characterized by low SOD activity are advantageously treated using a copper salicylate complex in combination with known anti-cancer drugs. For example, a treatment mixture containing both CuDIPS and bis-dichloroethy-N-nitroso urea (BCNU) is effective in prolonging survival of tumor-bearing host organisms, 2 Oberley, L. W., (unpublished observation).

It has not been possible to discern the mechanism by which CuDIPS effects its antitumor activity. The mechanism is just not known. However, this mechanism is not crucial to the advantageous practice of this invention. The following discussion merely postulates what are believed to be mechanisms that could describe the activity.

There are at least five different mechanisms by which CuDIPS could work: (1) cytotoxicity; (2) immune cell mediated effects; (3) antibody mediated effects; (4) inhibition of cell proliferation without cell differentiation; (5) inhibition of cell proliferation with differentiation. Cytotoxicity appears to be unimportant. Because tumors were not infiltrated with any type of inflammatory cell, the second mechanism also appears to be unimportant. Thus, either antibody mediated effects or inhibition of cell proliferation with or without differentiation appear to cause the following observed effects. These effects are unexpectedly opposite to the effects of other copper compounds that have been shown to treat cancer by killing tumor cells.

FIG. I shows the reduction of tumor size over time with mice treated with Orgotein.

FIG. II shows the survival time of tumor bearing mice treated with Orgotein.

FIG. III shows the difference in tumor growth when the tumor bearing mice are treated with CuDIPS for five days.

FIG. IV shows the survival curves of CuDIPS-treated groups.

FIG. V and FIG. VI show that the compounds Cu(II) (salicylate)$_2$-CuS, CuDIPS and Cu(II) (3,5 ditertiarybutylsalicylate)$_2$-CuDTBS dramatically reduced tumor growth and prolonged survival of the host organisms.

FIG. VII and FIG. VIII show that the Cu(II)$_2$ (aspirinate)$_4$ reduces tumor growth and increases survival of the animals bearing Ehrlich tumors.

FIG. IX shows efficacy of various copper salicylate complexes for inhibition of tumor growth.

BEST MODE FOR CARRYING OUT THE INVENTION

Orgotein, a generic name for CuZnSOD derived from bovine liver, is obtained from Diagnostic Data Incorporated, Mountain View, California. It is 98% pure CuZnSOD isolated from bovine liver and had 3,300 units of pure erythrocyte SOD activity/mg protein when assayed by the method of Beauchamp, C. and Fridovich, I., *Superoxide Dismutase: Improved Assays and an Assay Applicable to Acrylamide Gel.,* Anal. Biochem. 44:276-287 (1971), hereby incorporated by reference. Orgotein was dissolved in USP grade nonpyrogenic sterile saline.

CuDIPS is synthesized using known methods. Sorenson, J. R. J., *Copper Chelates as Possible Active Forms of the Antiarthritic Agents,* J. Med. Chem. 19:135-148 (1976); Sorenson, J. R. J., *Some Copper Coordination Compounds and their Antiinflammatory and Antiulcer Activities,* Inflammation 1:317-331 (1976), hereby incorporated by reference. CuDIPS is lipid soluble, and the $LD_{50}$ is 240±33 mg/kg when administered subcutaneously to rats. CuDIPS is suspended in 10% Tween 80-saline ((Z) Sorbition mono-9-ocladecinoate poly-(oxy-1,2-ethonediyl)) solution.

The SOD activity of Orgotein and of tumor homogenates is assayed by the method of Beauchamp and Fridovich. Reaction mixtures contain 0.05M potassium phosphate buffer (pH 7.8) with $10^{-3}$M diethylenetriaminepentaacetic acid, $10^{-4}$M of xanthine, $5.6 \times 10^{-5}$M of nitro blue tetrazolium, $10^{-3}$ units of xanthine oxidase and 1 unit of catalase. Addition of $5 \times 10^{-3}$M NaCN to this mixture inhibits CuZnSOD activity and allows the measurement of the activity of the cyanid insensitive MnSOD alone. The rate of blue formazan formation is measured by following the change of absorbance at 560 nm with a Cary Model 15 spectrophotometer. The sensitivity of the assay was such that 1 unit equaled 14±1 ng of pure erythrocyte SOD. The amount of protein in each sample is assayed using a conventional method. Tissue homogenates are prepared by excising tumor mass from mice implanted with Ehrlich carcinoma cells. After bones and muscles are removed, the tumor tissue is rinsed and minced in 0.05 M potassium phosphate buffer (pH 7.8) and homogenized in a motor-driven Teflon pestle homogenizer. $O_2^-$ scavenging ability of CuDIPS is determined by a similar assay method; the only difference is that dimethyl sulfoxide (DMSO) solvated potassium superoxide ($KO_2$) is used to generate $O_2^-$ instead of xanthine and xanthine oxidase. CuDIPS is dissolved in 10% Tween 80-saline. This alternate method is chosen due to the length of previous procedure and lipid insolubility of some of the reactants of the previous assay. Free $O_2^-$ is released when DMSO-$KO_2$ is added to an aqueous solution. Reaction mixtures contain 1:20 dilution of a saturated $KO_2$ solution (20 mg $KO_2$/ml of dimethyl sulfoxide), $5.6 \times 10^{-5}$M of nitro blue tetrazolium, 1 unit of catalase and 0–500 μg of CuDIPS in 0.5 M potassium phosphate buffer, pH 7.8. The formation of blue formazan is determined by recording the final absorbance of the assay mixture at 560 nm with a Cary Model 15 spectrophotometer. The sensitivity of this assay is found to be 0.85 μg of pure bovine SOD per unit of activity.

Tumor models used in these experiments are Sarcoma 180 cells implanted in 8–12 week old standard CF1 female mice (Charles River Breeding Laboratory, Wilmington, Massachusetts) and Ehrlich carcinoma cells implanted in standard CBA/J female mice (Jackson Laboratory, Bar Harbor, Maine). The tumor cells are maintained intraperitoneally in their respective hosts and are harvested and transferred weekly. Peritoneal fluid from these tumor hosts are centrifuged at 420 xg for 2 minutes; the pellet is resuspended and washed three times in isotonic saline. The resulting pellet is diluted 1:5 with isotonic saline. Cell counts are done using a Coulter Model B cell counter. Solid tumors are induced by implanting $5 \times 10^6$ cells intramuscularly into the right thigh of their respective hosts. Tumor growth is estimated by two dimensional measurements of the tumor thigh; group means and standard error of the means are plotted. The significance of differences between tumor growth curves is determined by a conventional Student's t-tests. Survival curves are analyzed by a conventional Mantel-Cox's Generalized Savage Test and a conventional Breslow's Generalized Wilcoxan test. The p values (probability that observation is due to chance alone) reported are the higher of the p values from these 2 tests.

The antitumor activity of Orgotein is studied in both tumor models. A dose of 1.2 mg of Orgotein in 0.15 ml Tween 80-saline is injected intramuscularly at the tumor site. A single dose is given to animals implanted with Sarcoma 180 cells at 1 hr, 5 days or 10 days after transplantation. Mice implanted with Ehrlich carcinoma cells are also treated with Orgotein. 5 or 10 daily doses are administered instead of a single dose; Tween 80-saline treated mice are used as control. Antitumor activity of CuDIPS is examined in mice with Ehrlich carcinoma only. A daily dose of 0.5 or 1.0 mg in 0.2 ml of Tween 80-saline is administered intramuscularly at the tumor site for 5 days, 10 days, or every Monday, Wednesday, and Friday for a total of 10 or 18 doses with the first dose administration at 1 hr following implantation of tumor cells. Another treatment schedule includes 5 daily doses beginning immediately after transplantation and an additional 5 daily doses starting on the 35th day after transplantation. Each treatment group consists of 24 tumor bearing mice. Tween 80-saline injected mice are used as controls.

Autopsies are performed on all dead animals. Tissues from the tumor masses and organs are excised and processed by known histologic techniques and stained with hematoxylin and eosin.

Antitumor Activity of Orgotein

Orgotein is administered to CF1 and CBA mice one hour after intramuscular implantation of Sarcoma 180 cells and Ehrlich carcinoma cells, respectively. As shown in Table I, tissue homogenates from these two types of solid tumor contain reduced amounts of total SOD activity and diminished amounts of MnSOD activity as compared to that from normal leg muscle of the mice without tumor cell implantation. Thus, these models appear to be representative in their SOD activity of the total class of tumors.

TABLE I

| SOD ACTIVITIES IN TISSUE HOMOGENATES (Units/mg protein)* | | |
|---|---|---|
| | Total SOD | Mn SOD |
| Normal leg muscle | 45 ± 3(4)** | 14 ± 1 |
| Sarcoma 180 | 39 ± 6(7) | less than 2 |
| Ehrlich carcinoma | 27 ± 2(13) | less than 2 |

*Sarcoma 180 and Ehrlich carcinoma tissues are excised between 5 and 45 days after transplantation, minced and homogenized in 0.05M potassium phosphate buffer (pH 7.8). Little difference in activity are observed between days 5 and 45, so the values obtained are averaged. Normal leg muscle tissue are treated in a similar fashion. SOD activity is measured by the conventional xanthine-xanthine oxidase nitro blue tetrazolium method. Errors represent standard error.
**Number of animals sampled.

Orgotein is assayed to have 49,500±300 units of SOD activity/mg protein by the xanthine-xanthine oxidase method. When 1.2 mg of Orgotein is given to mice with Sarcoma 180 tumors at 1 hour after tumor cell implantation, a reduction in tumor size is observed, as indicated in Chart I (p less than 0.05 between 11 and 27 days); after 27 days, the growth curves are the same.

Table II and Chart II show the survival times of these tumor bearing mice; there is a 23% increase in mean survival time in the Orgotein treated group (p less than 0.1). Viability of the Sarcoma 180 cells ($2.5 \times 10^7$ cells/ml) is unchanged when they are incubated in 0.8 mg/ml Orgotein for one hour, showing that the effect of Orgotein is probably not due to cytotoxicity.

TABLE II

| EFFECT OF ORGOTEIN TREATMENT ON SURVIVAL OF CF1 MICE IMPLANTED WITH SARCOMA 180 CELLS | | | |
|---|---|---|---|
| Treatment Group | Mean Survival Time in Days | Median Survival Time in Days | Maximum Survival Time in Days |
| Saline | 41 ± 5* | 46 | 82 |
| Orgotein | 53 ± 5 | 53 | 90 |

*standard error

Tumors developed from those cells treated with Orgotein show no difference histologically from those developed from untreated cells. Histologic studies of the tumors from the Orgotein treated group show evidence of the development of a prominent fibroblast response in the area surrounding the tumor in some, but not all, of these animals on the 5th day after inoculation of tumor cells. An infiltrative pattern of growth is noted from tumors in the saline control mice.

When Orgotein at the same dose is given to mice transplanted 5 or 10 days earlier with Sarcoma 180 solid tumor, no significant decrease in tumor growth or increase in survival is observed compared to the saline treated control. Ehrlich carcinoma cells implanted in CBA mice also do not respond to Orgotein treatment administered on the day of implantation or for 5 or 10 consecutive days afterwards.

Antitumor Activity of CuDIPS

When SOD activity is measured by the method of DMSO-$KO_2$, CuDIPS has a mean of 17,400±1,800 units of SOD activity/mg of the compound, but the ligand DIPS alone, possesses no $O_2^-$ scavenging ability. When Ehrlich carcinoma cells ($25 \times 10^7$ cells/ml) are incubated with 5 mg/ml of CuDIPS for one hour, no toxicity is indicated. Preliminary dose study indicates that about 0.5 to 1.0 mg of CuDIPS gives a maximum effect without causing toxicity to animals. For this reason, a dose of 0.5 or 1.0 mg is always used. Chart III shows the difference in tumor growth when the tumor bearing mice are treated with CuDIPS (p less than 0.001) for 5 days.

Approximately the same growth curve is obtained for all other treatment groups.

Table III summarizes the differences in survival times in the various treatment groups (p less than 0.0001 for all groups). Chart IV shows the survival curves of CuDIPS-treated groups.

TABLE III

EFFECT OF CuDIPS TREATMENT ON SURVIVAL OF CBA MICE IMPLANTED WITH EHRLICH CARCINOMA CELLS

| Treatment Group | Mean Survival Time in Days | Median Survival Time in Days | Maximum Survival Time in Days |
|---|---|---|---|
| Tween-80 × 5** (Daily) | 33 ± 4* | 33 | 53 |
| CuDIPS × 5 (Daily) | 54 ± 3 | 52 | 68 |
| CuDIPS × 10 (Daily) | 58 ± 5 | 55 | 87 |
| CuDIPS × 18 (MWF × 6) | 50 ± 4 | 49 | 79 |
| CuDIPS × 10 (MWF) | 61 ± 6 | 62 | 124 |
| CuDIPS × 10 (Daily, days, 0–4 and 35–39) | 58 ± 4 | 59 | greater than 124 |

*standard error
**total number of injections

All treatment shows a similar effect on survival of the mice, but the group that received 0.5 mg of CuDIPS on Mondays, Wednesdays, and Fridays for a total of 10 doses showed a greater increase in mean survival. Out of 24 mice in this group, two of them had regressed tumors; however, the tumors recurred by 90 days after the initial implantation. Autopsies are performed on all dead mice. It is found that all animals died from massive lung metastases. Histologic studies of the organs of the tumor bearing mice revealed that microscopic nodules of tumor cells are present in the lung of the control mice as early as 10 days after implantation of cells, but microscopic lung metastasis are not observed in the CuDIPS treated mice until 45 days after transplantation of the tumor cells. Histologic studies of the tumor from the CuDIPS treated mice show tumors are not infiltrated by any type of inflammatory cell.

$CuSO_4$ at a dose of 0.5 mg in 0.1 ml of Tween 80-saline is also given to CBA mice implanted with Ehrlich carcinoma cells for 5 days after transplantation. A continuous loss of weight of the tumor bearing mice is observed and death is caused by massive lung metastasis. In contrast to the above results, no weight loss was observed when mice are treated with various doses of CuDIPS, indicating that its effects are most likely not due to toxicity of the copper compounds.

Another group of CBA mice implanted with Ehrlich carcinoma cells received intramuscular injections of single doses of DIPS. No apparent SOD-like activity is exhibited by the DIPS and loss of body weight followed by death due to extensive lung metastasis is observed in the hosts.

$CuSO_4$ or DIPS alone have no antitumor activity. These observations demonstrate that the antitumor effects of CuDIPS is independent of and not attributable to any activity of its respective Cu or DIPS components.

The results indicate that the two tumor models chosen did indeed have a reduced level of both CuZn-SOD and MnSOD activity. When this lost SOD activity is replaced by the local injection of Orgotein, a slight effect on the tumor growth and survival is observed in case of Sarcoma 180 tumor cells. Ehrlich carcinoma in CBA mice, however, did not respond to Orgotein treatment. Preliminary experiments with standard Swiss mice implanted with Erhlich carcinoma cells indicated that a reduction in tumor size occurs in the Orgotein treated mice. CBA mice are able to acquire immunologic tolerance; this may have contributed to the lack of response to the Orgotein treatment. Another possible explanation for the observed differences in response is that under certain conditions, the tumor cells may be able to take in SOD by phagocytosis. Thus, a small amount of the enzyme may get in the cell or Orgotein may represent a source of copper complexes which can be utilized by cells. In any case, Orgotein does not have a large effect on the growth of tumor cells in any of the models studied.

Other copper compounds have antineoplastic activity which prolongs survival of tumor bearing mice. Most of these compounds are cytotoxic; they prevent the development of tumors by cell killing.

CuDIPS has been shown to be a potent anti-inflammatory agent. This compound is also non-toxic to the host at the dose levels used. The advantage of this $O_2^{-}$ scavenger over Orgotein is its small molecular size, which enables it to penetrate cell membranes and enter organelles, thus replacing the lost SOD activity within the tumor cells. The reduction in the size of the Ehrlich carcinomas in CBA mice after treatment with CuDIPS means that CuDIPS has a marked beneficial effect on this tumor model. Because Orgotein exerts no effect on tumor growth in this model, and both compounds are $O_2^{-}$ scavengers, these different antitumor activities may be due to differences in ability to penetrate cell membranes. Thus, intracellular localization of the added $O_2^{-}$ scavengers may be responsible for the observed antitumor effect.

Due to the heterogeneous nature of tumors, various types of tumors respond to the CuDIPS therapy differently. In all CuDIPS treated tumor mice, tumor growth retardation occurs; however, the reduction of tumor size is unaffected by the total dose administered. This could be due to the fact that the CuDIPS sensitive cell populations are eliminated at a certain dose level; different regimens may be required to achieve additional beneficial therapeutic effects.

Growth Inhibition and Morphological Differentiation Effects of CuDIPS On Neuroblastoma Cells CuDIPS inhibits cell population growth and induces morphological differentiation of mouse neuroblastoma-cells in vitro.

The neuroblastoma cell clone $NBP_2$ provided by Dr. K. N. Prasad (University of Colorado), is maintained according to the procedure of Prasad and Hsie, Prasad, K. N. and Hsie, A. N., *Nature New Biol.* 233:141 (1971), hereby incorporated by reference. Cells are grown as a monolayer in 75 cm$^2$ Falcon plastic tissue culture flasks containing F-12 medium supplemented with 10% gamma globulin-free new born calf serum, penicillin (100 U/ml) and streptomycin (100 μg/ml). Cultures are maintained in a humidified atmosphere of 5% $CO_2$ in a water jacketed incubator at 37° C. The cells are harvested with 0.25% Pancreatin and washed twice with fresh medium for subsequent plating. Only exponentially growing cells are used in the experiment. The viability of attached cells, determined 3 days after treatment by exclusion of trypan blue dye in control and treated cells, regularly exceeds 90%. Medium, serum, antibiotics, and pancreatin are purchased from Grand Island Biological Company.

CuDIPS was synthesized using known methods. Fifty-thousand cells were seeded in each 60 mM plastic petri dish containing 5 ml of the growth medium. Cells are treated with CuDIPS 24 hours after seeding. CuDIPS is dissolved in ethanol to give a final concentration of 10, 25, or 50 μg/ml of copper compound in the medium. The concentration of ethanol in the medium is kept constant at 1% in all the treated and control dishes. Culture dishes containing 1% ethanol serve as controls. One day after the start of treatments and daily afterwards, fresh drug and medium are provided in each dish. To avoid possible degradation, CuDIPS is dissolved in ethanol immediately before use. The experiment is done in triplicate. Three days after the initial treatments the number of cells and percent differentiation of cells are scored in each dish. Four hundred cells per culture dish from at least three different regions are examined with a Leitz Divert phase contrast microscope. Cells with one or more processes at least twice as long as the soma diameter (processes usually longer than 50 microns) are scored as differentiated. To count the number of cells, cells are harvested with Pancreatin and the number of cells in each dish is determined by counting cells in a hemocytometer.

The effects on cell population and the percentage of morphological differentiation after three days of treatment with various concentrations of CuDIPS are observed and are summarized in Table IV.

| Treatments | Cell number* $\times 10^5$ | % differentiation** |
|---|---|---|
| Control | 17.1 ± 1.9 | 8.0 ± 3.7 |
| Cu(II)(3,5-diisopropyl-salicylate)$_2$ | | |
| 10 μg/ml | 12.7 ± 1.4 | 7.4 ± 2.6 |
| 25 μg/ml | 7.1 ± 1.2 | 22.4 ± 2.6 |
| 50 μg/ml | 1.4 ± 0.6 | 74.2 ± 4.9 |

*Each value represents mean of 24 determinations.
**Each value represents 9 determinations, at least 300 cells were counted in each dish. The experiment is conducted in triplicate and each value is given as mean ± S.D.

Three days after treatment with the CuDIPS at 10 ug/ml concentration, a small reduction in the number of cells per culture dish is observed. The decrease in cell population is significant (p less than 0.05, Student's t-test). This level of concentration of CuDIPS caused no significant change in the percentage of differentiated cells. Treatment with 25 μg/ml of CuDIPS reduces the cell population to $(7.1 \pm 1.2) \times 10^5$ cells/culture dish, a figure which represents less than half of the cell population found in conrol. At a concentration of 50 μg/ml, CuDIPS causes a remarkable reduction in cell population. Higher concentrations of CuDIPS (75 or 100 μg/ml) are toxic to cells and kills almost all cells in 3 days of treatments. No floating or dead cells are observed in the culture dishes which receive the copper compound to a maximum concentration of 50 μg/ml.

CuDIPS also induces morphological differentiation in neuroblastoma cells. Although the induction of differentiation is not observed at a concentration of 10 μg/ml, at a concentration level of 25 μg/ml, 22.4±2.6 percent of the neuroblastoma cells differentiated. A treatment concentration of 50 μg/ml, produces an average of 74.2±4.9 percent differentiated cells after 3 days of treatment. This represents more than 9 times the percentage of differentiated cells in controls. The majority of cells treated with 50 μg/ml of CuDIPS morphologically resembles mature neural cells.

Antineoplastic Activities of Copper Salicylates

A variety of copper salicylate complexes exhibit antineoplastic activity in CBA/J female mice implanted with Ehrlich carcinoma cells. The degree of tumor growth inhibition positively correlated with the degree of lipid solubility of the particular copper salicylate complex.

Tumors are induced in inbred CBA/J female mice (The Jackson Laboratory, Bar Harbor, Maine) by implantation of Ehrlich carcinoma cells. Tumor cells are maintained intraperitoneally in their hosts and are harvested and transferred weekly. Solid tumors are induced by intramuscular injections of $5 \times 10^6$ cells into the right thighs of hosts. Cells are enumerated with a Coulter Model B counter. Tumor growth is estimated by two-dimensional measurements of the thighs; group means and standard errors are calculated. The significance of differences between tumor growth curves is determined by Student's t-Tests for particular times. Survival curves are analyzed by Mantel-Cox's generalized Savage Test and Brelow's generalized Wilcoxon Test. The p-values reported are the higher values from these two tests. For survival data, p-values represent differences between complex treated and Tween 80-saline treated control groups over the whole curve and not at a particular time.

Copper salicylates are synthesized by known methods. Aqueous solutions of sodium salicylates are prepared by combining equivalent amounts of sodium hydroxide and the corresponding salicylic acid. To this solution is added 0.5 equivalents of copper chloride. The resulting precipitates are collected by filtration, washed with water, dried in vacuo for 24 hours at 50°, and submitted for elemental analysis. The analytical values agree with the calculated values within±0.4%.

Mice implanted with Ehrlich carcinoma cells are treated with copper chelates suspended in 10% Tween 80-saline solution just prior to administration. All treatments are delivered by 0.1 ml intramuscular injections at the site of cell implantation. A daily dose of 0.5 to 1.0 mg copper chelate in 0.1 ml of 10% Tween 80-saline is administered for 5 days, 10 days, or every Monday, Wednesday, and Friday for a total of up to 12 doses, with the first dose given 1 hour after inoculation of cells. Another schedule includes five daily doses beginning 1 hours after transplantation. Each treatment group consists of 24 tumor-bearing mice. Mice given Tween 80-saline injections are used as controls.

The data presented in Charts V and VI show that each of the following copper compounds:
Cu(II)(salicylate)$_2$-CuS
CuDIPS
Cu(II)(3,5-ditertiarybutylsalicylate)$_2$-CuDTBS
dramatically reduced tumor growth and prolonged survival of the host organisms.

On the 58th day after implantation, all of the control animals died, but there were surviving hosts in each of the complex-treated groups. 25% of the CuDTBS-treated, 30% of the CuS-treated, and 45% of the CuDIPS-treated mice survived beyond the time at which all of the control mice died. In addition, the period for 100% survival increased as compared to controls for all of the treated groups and the longest period was ten times longer, 44 days, for the CuDTBS-treated group. More than 90% of the animals treated with CuDIPS survived for 48 days. Lastly, when CuDIPS was given every day for 10 days, 10% of the animals survived for over 98 days, Leuthauser, S. W. C., Oberley, L. W. Oberley, T. D., Sorenson, J. R. J., and Ramakrishna, K., *Antitumor Effect of a Copper Coordination Compound with Superoxide Dismutase-Like Activity*, J. Nat'l. Cancer Inst. 66:1077–1081 (1981), hereby incorporated by reference. Lung metastasis was markedly reduced in the copper complex treated mice.

The observed antineoplastic activity must be attributed to the complexed form of copper because copper sulfate and diisopropylsalicylic acid are shown to have no antitumor effect in this Ehrlich tumor model, Oberley, L. W., Leuthauser, S. W. C., Oberley, T. D. Sorenson, J. R. J. and Pasternack, R. F., *"Antitumor Activities of Compounds with Superoxide Dismutase Activity"* in *Roles of Copper and Other Essential Metalloelements in Inflammatory Diseases*, Human Press, Clifton, New Jersey, pp. 423–433 (1982), hereby incorporated by reference.

Antitumor Activity of Copper Acetylsalicylate Complexes

The activity of various copper acetylsalicylate compounds is also tested. As shown in Charts VII and VIII, the copper complex of aspirin, $Cu(II)_2(aspirinate)_4$, reduces tumor growth and increases survival of the host. This complex is more active than SOD, because the latter has no effect against this solid Ehrlich tumor.

Tests involving other copper salicylate complexes reveal that they are more effective than the copper aspirinate compound, producing a further inhibition of tumor growth, as shown in Chart IX. The copper salicylate complexes compounds tested include:
$Cu(II)_2(aspirinate)_4(DMSO)_4$,
$Cu(II)_2(aspirinate)_4(pyridine)_4$; and
$Cu(II)(3,5\text{-diisopropylsalicylate})_2(CuDIPS)$.

Among the copper complexes shown in Chart IX, increased lipid solubility appears to be related to increased antitumor activity. $Cu(II)(3,5\text{-diisopropylsalicylate})_2(CuDIPS)$, having the highest degree of lipid solubility of the tested compounds, is found to be most effective in reducing tumor growth.

Cytoxicity does not appear to account for the effectiveness of these complexes, because their $LD_{50}$ values are much larger than the dosages used in the experiments. The effective dose of $Cu(II)_2(aspirinate)_4$ is 50 mg/kg following intramuscular administration, while its $LD_{50}$ is determined to be 760 mg/kg in rats and greater than 320 mg/kg in mice, following subcutaneous injection. An intramuscular dose of 25 mg/kg of CuS is found to be an effective dose, while $LD50$ values of 440 mg/.kg, and greater than 320 mg/kg were reported following subcutaneous administration to mice, Sorenson, J. R. J., Rauls, D. O., Ramakrishna, K. Stull, R. E. and Voldeng, A. N., "Anticonvulsant Activity of Some Copper Complexes" in *Trace Substances in Environmental Health*, XIII University of Missouri Press, Columbia, Mo, pp. 360–367 (1979). Similarly, the effective intramuscular dose of CuDIPS is 25 mg/kg while reported $LD_{50}$ values are 240 mg/kg in rats and greater than 320 mg/kg in mice following subcutaneous administration. Also, if these complexes cause cell death, a significant number of normal muscle cells would have been killed with treatment. Finally, there is no difference in the number of cells killed when Ehrlich cells were incubated at 37° C. for one hour with medium containing 5 mg of CuDIPS per milliliter of saline.

In the treatment of human cancer patients, the copper complexes would be administered to patients in dosages and according to regimens that would be therapeutically effective in replacing lost SOD activity in the cancerous cells.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

We claim:

1. A method for treating cancer types in mammals, said cancer types being characterized by abnormal superoxide dismutase activity, comprising administration to a mammal having a tumor characterized by abnormal superoxide dismutase activity of a therapeutically effective amount of a copper salicylate complex and an anti-cancer drug.

2. A method for treating cancer types in mammals, said cancer types being characterized by abnormal levels of superoxide dismutase activity, comprising administration to a mammal having a tumor characterized by abnormal superoxide dismutase activity of a therapeutically effective amount of (i) a copper salicylate complex selected from the group consisting of $Cu(II)(salicylate)_2$, $Cu(II)(3,5\text{-diisopropylsalicylate})_2$, $Cu(II)(3,5\text{ ditertiarytbutylsalicylate})_2$, $Cu(II)_2(aspirinate)_4(pyridine)_4$ and $Cu(II)_2(aspirinate)_4(DMSO)_4$ and (ii) an anti-cancer drug.

3. The method according to claim 2, wherein the anti-cancer drug is bis-dichloroethyl-N-nitroso urea.

4. A method for treating cancer types in mammals, said cancer types being characterized by abnormal superoxide dismutase activity, comprising administration to a mammal having a tumor characterized by abnormal superoxide dismutase activity of a therapeutically effective amount of $Cu(II)(3,5\text{ ditertiarybutylsalicylate})_2$ and bis-dichloroethyl-N-nitroso urea.

5. The method according to claim 2, wherein the cancer type is Ehrlich carcinoma.

6. The method according to claim 4, wherein the cancer type is Ehrlich carcinoma.

7. The method according to claim 2, in which the composition is administered intramuscularly.

8. The method according to claim 2, in which the composition is administered intravenously.

9. The method according to claim 2, in which the composition is administered subcutaneously.

10. The method according to claim 2, in which the composition is administered topically.

11. The method according to claim 2, in which the composition is administered orally.

12. The method according to claim 2, in which the composition is administered intraperitoneally.

13. The method according to claim 4, in which the composition is administered intramuscularly.

14. The method according to claim 4, in which the composition is administered intravenously.

15. The method according to claim 4, in which the composition is administered subcutaneously.

16. The method according to claim 4, in which the composition is administered topically.

17. The method according to claim 4, in which the composition is administered orally.

18. The method according to claim 4, in which the composition is administered intraperitoneally.

* * * * *